United States Patent
Castillo et al.

(10) Patent No.: US 11,382,546 B2
(45) Date of Patent: Jul. 12, 2022

(54) PSYCHOPHYSICAL PERFORMANCE MEASUREMENT OF DISTRIBUTED APPLICATIONS

(71) Applicant: CA, Inc., Islandia, NY (US)

(72) Inventors: Ross Castillo, Islandia, NY (US); Satish Kumar Naidi, Telangana (IN)

(73) Assignee: CA, Inc., San Jose, CA (US)

( * ) Notice: Subject to any disclaimer, the term of this patent is extended or adjusted under 35 U.S.C. 154(b) by 1129 days.

(21) Appl. No.: 15/949,744

(22) Filed: Apr. 10, 2018

(65) Prior Publication Data

US 2019/0307386 A1 Oct. 10, 2019

(51) Int. Cl.
*A61B 5/16* (2006.01)
*A61B 5/145* (2006.01)
(Continued)

(52) U.S. Cl.
CPC ............ *A61B 5/165* (2013.01); *A61B 5/0077* (2013.01); *A61B 5/02055* (2013.01); *A61B 5/0533* (2013.01); *A61B 5/14546* (2013.01); *A61B 5/14551* (2013.01); *A61B 5/163* (2017.08); *A61B 5/369* (2021.01); *A61B 5/4803* (2013.01); *A61B 5/746* (2013.01); *H04L 67/1004* (2013.01); *A61B 5/021* (2013.01);
(Continued)

(58) Field of Classification Search
CPC ............... G06F 9/5083; G06F 11/0709; G06F 11/3006; A61B 5/165; A61B 5/0077; A61B 5/02055; A61B 5/0533; A61B 5/14546; A61B 5/14551; A61B 5/163; A61B 5/369; A61B 5/4803; A61B 5/746; A61B 5/021; A61B 5/024; A61B 5/0245; A61B 5/0816; H04L 67/1004
See application file for complete search history.

(56) References Cited

U.S. PATENT DOCUMENTS 9,852,011 B1 * 12/2017 Yemini .............. G06Q 10/0631
2008/0177994 A1 7/2008 Mayer
(Continued)

OTHER PUBLICATIONS

Wearables Want To Track Your Stress—But It's Really Hard To Do; BuzzFeed News, posted on Jul. 7, 2016, Retrieved from the Internet: URL: <https://www.buzzfeed.com/stephaniemlee/heres-why-its-hard-for-wearables-to-actually-track-your-stre?utm_term=.vhpRZKq4x#.hu5jw18KR> [Retrieved on Feb. 23, 2018], 9 pages.

(Continued)

*Primary Examiner* — Ryan W Sherwin
(74) *Attorney, Agent, or Firm* — Adsero IP

(57) ABSTRACT

Provided is a process including: receiving biometric measurements; receiving from application components or network hosts, events or metrics indicative of objective performance; correlating psychophysical-performance values based on the biometric measurements indicative of psychophysical performance with objective-performance values based on the events or metrics indicative of objective performance; storing the correlation between the psychophysical-performance values and the objective-performance values in memory; and accessing the correlation to select hosts, application components, or routines to be adjusted to improve objective performance of the distributed application or psychophysical performance of the distributed application.

20 Claims, 4 Drawing Sheets

(51) Int. Cl.
    *A61B 5/0533*     (2021.01)
    *A61B 5/1455*     (2006.01)
    *A61B 5/00*     (2006.01)
    *H04L 67/1004*     (2022.01)
    *A61B 5/0205*     (2006.01)
    *A61B 5/369*     (2021.01)
    *A61B 5/0245*     (2006.01)
    *A61B 5/024*     (2006.01)
    *A61B 5/021*     (2006.01)
    *A61B 5/08*     (2006.01)

(52) U.S. Cl.
    CPC .............. *A61B 5/024* (2013.01); *A61B 5/0245* (2013.01); *A61B 5/0816* (2013.01)

(56) References Cited

U.S. PATENT DOCUMENTS

| | | | | |
|---|---|---|---|---|
| 2010/0161810 A1* | 6/2010 | Vaidyanathan | ..... | G06F 11/3006 709/228 |
| 2011/0078227 A1* | 3/2011 | McAloon | .............. | G06F 16/284 709/224 |
| 2013/0041590 A1* | 2/2013 | Burich | ................ | G06F 11/3006 702/19 |
| 2013/0212440 A1* | 8/2013 | Rom | .................... | G06F 11/0751 714/47.1 |
| 2013/0246001 A1* | 9/2013 | Uchida | ............... | G06F 11/0709 702/182 |
| 2014/0344718 A1 | 11/2014 | Rapaport et al. | | |
| 2016/0266962 A1* | 9/2016 | Rajasekharan | ....... | H04L 41/142 |
| 2017/0043166 A1 | 2/2017 | Choi et al. | | |
| 2017/0239130 A1 | 8/2017 | Rizzo | | |
| 2017/0243465 A1* | 8/2017 | Bourne, Jr. | ............ | G08B 21/24 |
| 2017/0249200 A1* | 8/2017 | Mustafi | ............... | G06F 11/0709 |
| 2017/0330023 A1 | 11/2017 | Gordon et al. | | |
| 2018/0097825 A1* | 4/2018 | Pavlas | ................. | G06F 11/0751 |
| 2019/0155672 A1* | 5/2019 | Wang | .................. | G06F 11/0751 |
| 2019/0163528 A1* | 5/2019 | Zhou | ................... | G06F 11/3442 |

OTHER PUBLICATIONS

Schall, A., "The Future of UX Research: Uncovering the True Emotions of Our Users," User Experience—The Magazine of th User Experience Professionals Association, published Apr. 2015, Retrieved from the Internet: URL: <https://uxpamagazine.org/the-future-of-ux-research/>, [Retrieved on Feb. 23, 2018], 16 pages.

"Psychophysics," Wikipedia, page last edited Dec. 5, 2017, Retrieved from the Internet: URL: <https://en.wikipedia.org/wiki/Psychophysics>, [Retrieved on Feb. 23, 2018], 8 pages.

Berlin, D., Biometrics in UX Research: The Next Big Step, Big Design Conference, Sep. 19, 2015, Retrieved from the Internet: URL: <https://www.slideshare.net/Banderlin/biometrics-in-ux-research-the-next-big-step>, [Retrieved on Mar. 3, 2018, 32 pages.

"Usability tesing video games with biometrics," Spotless, Retrieved from the Internet: URL: <https://www.spotless.co.uk/insights/testing-video-games-with-biometrics/>, [Retrieved on Mar. 3, 2018], 7 pages.

* cited by examiner

PSYCHOPHYSICAL PERFORMANCE MEASUREMENT OF DISTRIBUTED APPLICATIONS

BACKGROUND

1. Field

The present disclosure relates generally to distributed computing and, more specifically, to psychophysical performance measurement of distributed applications.

2. Description of the Related Art

Distributed applications are computer applications implemented across multiple computers. The group of computers generally each execute at least part of the application's code and cooperate to provide the functionality of the application. Examples include peer-to-peer architectures and client-server architectures, in which a client computer cooperates with a server to provide functionality to a user. Examples also include an application having components replicated on multiple computers behind a load balancer to provide functionality at larger scales than a single computer. Some examples have different components on different computers that execute different aspects of the application, such as a database management system, a storage area network, a web server, an application program interface server, and a content management engine.

These applications can be characterized as a service composed of a variety of other services, which may themselves be composed of other services. Examples of a service include a component (e.g., one or more executing bodies of code) that communicates via a network (or loopback network address) with another component, often by monitoring a port of a network address of the computer upon which the service executes. Services composed of other services generally form a service hierarchy (e.g., a service tree) that terminates in leaf nodes composed of computing hardware each executing a given low level service. In some cases, a given node of this tree may be present in multiple trees for multiple root services.

As distributed applications have grown more complex in recent years, and the scale of computing loads has grown, many distributed applications have been designed (or redesigned) to use more, and more diverse, services. Functionality that might have previously been implemented within a single thread on a single computing device (e.g., as different sub-routines in a given executable) has been broken-up into distinct services that communicate via a network interface, rather than by function calls within a given thread. Services in relatively granular architectures are sometimes referred to as a "microservice." These microservice architectures afford a number of benefits, including ease of scaling to larger systems by instantiating new components, making it easier for developers to reason about complex systems, and increased reuse of code across applications.

However, microservice architectures, and relatively complex distributed applications generally, give rise to a number of challenges for developers and operations engineers. Among other issues arising from increasingly complex systems, it can be very difficult to know where to focus resources when troubleshooting or improving upon distributed applications. Ultimately, such applications are often designed to provide some service to an end user, in many cases a human being. And it can be difficult to know which aspects of a distributed application affect the end user's subjective experience. For example, a relatively slow query applicable to one service may not be particularly aggravating for the end user given other context in the client-side application state, for example, if the query is running in service of some transaction that users expect to be slow or where the transaction is executed asynchronously with other operations that are faster and more important to the end-user's subjective experience. On the other hand, small adjustments in even a relatively fast transaction may impart relatively large effects on the end-user's subjective experience in other contexts. For example, changes in load times of certain websites have as small as 50 milliseconds been documented as having relatively large effects on user engagement with those websites. Thus, it can be difficult to know which aspects of the performance of a distributed application and the infrastructure on which it executes ultimately matter to end users (and to different types of end users), and as a result, it can be difficult to know where to allocate resources when adjusting such infrastructure and code of the distributed application to improve performance.

SUMMARY

The following is a non-exhaustive listing of some aspects of the present techniques. These and other aspects are described in the following disclosure.

Some aspects include a process including: receiving biometric measurements; receiving from application components or network hosts, events or metrics indicative of objective performance; correlating psychophysical-performance values based on the biometric measurements indicative of psychophysical performance with objective-performance values based on the events or metrics indicative of objective performance; storing the correlation between the psychophysical-performance values and the objective-performance values in memory; and accessing the correlation to select hosts, application components, or routines to be adjusted to improve objective performance of the distributed application or psychophysical performance of the distributed application.

Some aspects include a tangible, non-transitory, machine-readable medium storing instructions that when executed by a data processing apparatus cause the data processing apparatus to perform operations including the above-mentioned process.

Some aspects include a system, including: one or more processors; and memory storing instructions that when executed by the processors cause the processors to effectuate operations of the above-mentioned process.

BRIEF DESCRIPTION OF THE DRAWINGS

The above-mentioned aspects and other aspects of the present techniques will be better understood when the present application is read in view of the following figures in which like numbers indicate similar or identical elements.

Figure 1:
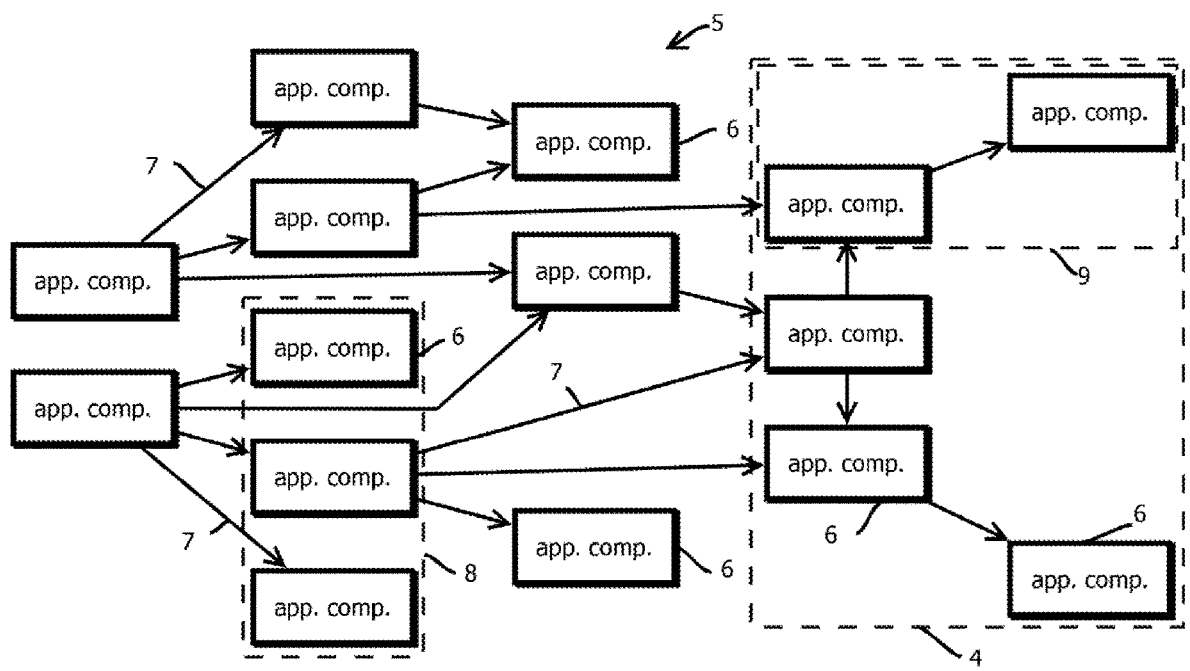
FIG. 1 is a block diagram of an example of a logical architecture of a distributed application that may be monitored in accordance with embodiments of the present techniques.

While the present techniques are susceptible to various modifications and alternative forms, specific embodiments thereof are shown by way of example in the drawings and will herein be described in detail. The drawings may not be to scale. It should be understood, however, that the drawings and detailed description thereto are not intended to limit the techniques to the particular form disclosed, but to the contrary, the intention is to cover all modifications, equivalents, and alternatives falling within the spirit and scope of the present techniques as defined by the appended claims.

DETAILED DESCRIPTION OF CERTAIN EMBODIMENTS

To mitigate the problems described herein, the inventors had to both invent solutions and, in some cases just as importantly, recognize problems overlooked (or not yet foreseen) by others in the fields of application and infrastructure monitoring and human-computer interaction. Indeed, the inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

Many existing monitoring applications monitor only individual computing device or system heath. These traditional systems typically take data from previously defined error criteria, such as high central processing unit (CPU) usage, high disk usage, or slow application responses. These systems are prone to errors or false positives during some normal user activity. In part this is because, these systems generally to not take a user's "feelings" or "frustrations" into account. If an application is working as "designed," but is not meeting the needs of a user, the system will generally not raise an alert.

Some embodiments mitigate these and other issues by integrating biometric data with system monitoring, in some cases, causing early alerts that allow service desk staff to contact a user before a problem ticket is raised. Some embodiments integrate biohealth with system health to create a proactive monitoring solution for computer systems. Some embodiments tailor monitoring around both the health of specific humans and the computer system being used. Some embodiments integrate user bio-health, computer health, and traditional help desk systems in such a way that alerts are proactively raised, and users are proactively contacted when problems are sensed on their computer, network, or connected peripherals as well as when the system detects high pulse rates, or high blood pressure that are beyond normal operating boundaries.

Some embodiments connect both human and system health monitoring to create a proactive stress-informed computing end user experience. Some embodiments are pre-emptive in their detection of systems failures, by incorporating human biometrics such as heart rate and blood pressure into monitoring. This biometric monitoring is expected to add a human factor to the system. Additional historical data may add baselines against which real-time (e.g., within less than 15 minutes of being measured) measurements are compared to allow a better experience over time.

In some embodiments, these techniques and others may be implemented on a distributed application with complexity like that described below with reference to FIG. 1 using a monitoring application and client-side biosensors like those described below with reference to FIG. 2. These approaches are best understood in view of the environment in which they may be deployed in some use cases. These and other issues may be mitigated by techniques exemplified below. It should be emphasized that some embodiments may implement only a subset of these techniques, as they are independently useful, or they may be used together.

The present techniques are better understood with an appreciation for the complexity of modern distributed applications. FIG. 1 shows an example logical architecture of a distributed application 5. This logical architecture is a relatively simple example used to illustrate the present techniques, so it should be appreciated that commercial embodiments are likely to process information related to substantially more complex distributed applications than that shown in FIG. 1.

In this example, the distributed application 5 includes 14 application components, but embodiments are expected to process monitoring information from distributed applications including substantially more application components, for example, exceeding 50, 100, and in some cases, 1000 different application components. In some cases, some of the application components are duplicate instances that operate concurrently, for instance, behind load balancers, to service transactions at larger scales. In some cases, there may be more than 50, 100, or 1000 different types of application components, with more than two, more than five, or more than 50 different instances of some of the different types.

In some embodiments, the distributed application 5 is partially or entirely implemented with a service-oriented architecture in which the different application components 6 are different instances of various services. In some cases, the services may be characterized as "microservices," a term used to refer to services in a relatively granular architecture in which the functionality of the distributed application is divided into a relatively large number of different services each having a relatively focused functionality. It is expected that industry will move towards increased use of microservices in the future, which is expected to make the above-describe problems even more acute. A species of this design pattern includes serverless architectures (which typically include servers but abstracts away management of the servers from workload application developers).

Each service is a different program or instance of a program executing on one or more computing devices. Thus, unlike different methods or subroutines within a program, the services in some cases do not communicate with one another through shared program state in a region of memory assigned to the program by an operating system on a single computer and shared by the different methods or subroutines. Rather, the different services may communicate with one another through network interfaces, for instance, by messaging one another with application program interface (API) commands (having in some cases parameters applicable to the commands) sent to ports and network addresses associated with the respective services (or intervening load balancers). In some cases, each port and network address pair refers to a different host, such as a different computing device, from that of a calling service. In some cases, the network address is a loopback address referring to the same computing device. Interfacing between services through network addresses, rather than through shared program state, is expected to facilitate scaling of the distributed application 5 through the addition of more computing systems and redundant computing resources behind load balancers. In contrast, often a single computing device is less amenable to such scaling as hardware constraints on even relatively high-end computers can begin to impose limits on scaling relative to what can be achieved through distributed applications.

In some cases, each of the services may include a server (e.g., an executed process) that monitors a network address and port associated with the service (e.g., an instance of a service with a plurality of instances that provide redundant capacity). In some embodiments, the server (e.g., a server process executing on the computing device) may receive messages, parse the messages for commands and parameters, and call appropriate routines to service the command based on the parameters. In some embodiments, some of the servers may select a routine based on the command and call that routine.

In some cases, the distributed application 5 may be characterized with a logical architecture topology like that shown in FIG. 1, which may indicate which application components call which other application components, as indicated by links 7 in the illustrated logical architecture topology. Further, in some cases, the logical-architecture topology may indicate groups of application components, such as group 8, that provide redundant capacity. In some cases, each application components 6 within group 8 may be a duplicate instance of the same service (which is not to imply that program state is identical at any given moment in time or that the instances are not configured differently, for instance, with different network addresses). In some cases, each application component in group 8 may provide the same service to calling application components. One group 8 of multiple instances of the same service is shown, but it commercial embodiments are expected to include many such groups, often with substantially more instances in each group. Often, to operate at commercially relevant scales, with acceptable uptimes, and acceptable latency, distributed applications include redundancy at all or nearly all services, as loads placed on the distributed application can fluctuate with time and individual computing devices and application components are expected to fail from time to time.

Further, in some cases, application components may be nested, as indicated by an application component 9 that includes two lower-level application components. Often, services are made up of other services, which may themselves be made from other services. In some cases, a given service may be part of multiple other services. Further, in some cases, a given service may be part of multiple distributed applications. In some embodiments, a hierarchy of services may be characterized by a service tree in which higher-levels in the tree call lower-levels in the tree in order to provide their respective service. In some cases, the service tree may include two, three, five, ten, or more different layers of hierarchy. For example, FIG. 1 shows another service 4 that includes service 9 along with several other application components 6 each providing a service, some of which are accessed directly by some other application components without a call to service 4.

The distributed application 5 may be any of a variety of different types of distributed applications, in some cases implemented in one or more data centers. In some cases, the distributed application is a software-as-a-service SaaS application, for instance, accessed via a client-side web browser or via an API. Examples include web-based email, cloud-based office productivity applications, hosted enterprise resource management applications, hosted customer relationship management applications, document management applications, human resources applications, Web services, server-side services for mobile native applications, cloud-based gaming applications, content distribution systems, and the like. In some cases, the illustrated distributed application 5 interfaces with client-side applications, like web browsers via the public Internet, and the distributed application 5 communicates internally via a private network, like a local area network, or via encrypted communication through the public Internet.

As discussed, distributed applications are often relatively complex and difficult for developers and operations engineers to reason about. To help make these applications more manageable, often monitoring applications are installed alongside the distributed application to gather information about the underlying computers upon which the distributed application is executing and performance of application components. However, as discussed above, it can be difficult to assess how different parts of the system affect the end-user's subjective experience or allocate resources in a manger that improves this aspect.

Figure 2:
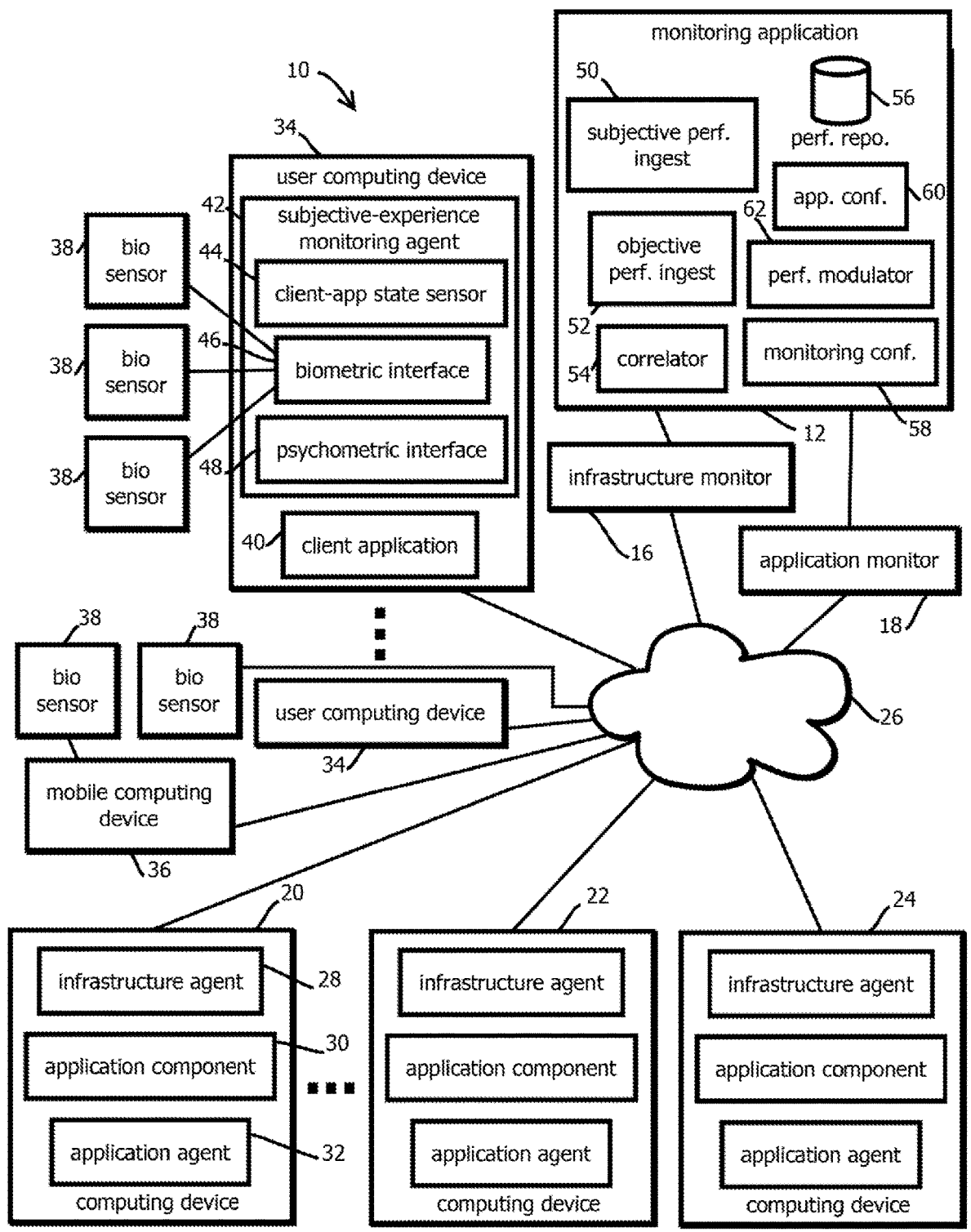
FIG. 2 is a block diagram of a computing environment having a monitoring application configured to monitor psychophysical performance of distributed applications in accordance with embodiments of the present techniques.

FIG. 2 shows an example of a computing environment 10 with a monitoring application 12 expected to mitigate this problem or address other problems discussed below or that will be apparent to a reader of ordinary skill in the art.

In some embodiments, the monitoring application 12 is operative to monitor both subjective and objective performance of one or more distributed applications. To this end, in some embodiments, the monitoring application 12 is configured to execute a process described below with reference to FIG. 3. In some embodiments, the components of the system of FIG. 2 may be implemented with a plurality of the computing devices like those described below with reference to FIG. 4, for instance, with rack-mounted computing devices in a data center or a plurality of data centers configured to communicate with one another via various networks, such as local area networks and the Internet.

In some cases, the monitoring application may route communicate via a different network than that of the distributed application. For instance, the monitoring application may communicate via an out-of-band network in a data center, while the distributed application may communicate via an in-band network. Out-of-band communications are expected to reduce an attack surface of the distributed application by maintaining at least some interfaces of the monitoring application on a network that is not exposed to the public Internet. Or in some cases, these communications may be consolidated on a single network, for instance to simplify the physical architecture.

The operation of the monitoring application 12 is best understood in view of the computing environment 10 in which it operates. In some embodiments, the computing environment 10 is a distributed computing environment including a relatively large number of computing devices, for instance, deployed over several data centers or enterprise local area networks. In many cases, the number of computing devices with which the computing environment 10 is implemented is expected to exceed 10, and in many commercially relevant use cases, 100, or 1000.

In this example, the computing environment 10 includes a monitoring application 12, an infrastructure monitor 16, an application monitor 18, a plurality of monitored computing devices 20, 22, and 24 executing a monitored distributed application, and a network 26, such as the Internet or various other intermediary networks, like local area networks. In some embodiments, the computing environment 10 may further include a plurality of user computing devices 34, mobile computing devices 36 of users, and biometric sensors 38.

Three computing devices 20, 22, and 24 are shown, but embodiments are expected to typically include many more, for instance, numbering in the dozens, hundreds, or thousands or more. In some embodiments, the computing devices 20, 22, and 24 may be rack-mounted computing devices in a data center, for instance, in a public or private cloud data center. In some embodiments, the computing devices 20, 22, and 24 may be geographically remote from one another, for instance, in different data centers, and geographically remote from the other components 12, 14, 16, and 18, or these components may be collocated.

In some embodiments, the network 26 includes the public Internet and a plurality of different local area networks, for instance, each within a different respective data center connecting to a plurality of the computing devices 20 through 24. In some cases, the various components may connect to one another through the public Internet via an encrypted channel. In some cases, a data center may include an in-band network through which the data operated upon by the application is exchanged and an out-of-band network through which infrastructure monitoring data is exchanged. Or some embodiments may consolidate these networks.

In some embodiments, each of the computing devices 20 through 24 may execute a variety of different routines specified by installed software, which may include application software, monitoring software, and an operating system. Application software, in this context, serves a different purpose from monitoring software. The application software generally executes in service of a business function or other workload for which the computing environment 10 was provisioned by a user. In contrast, the monitoring software monitors, and in some cases manages, the operation of the application software or the computing devices upon which the application software is executed. Thus, the application software does not require the monitoring software to serve its purpose, but with the complexity of modern application software and infrastructure, often the monitoring software makes deployments much more manageable and easy to improve upon.

In some cases, the application software is a distributed application, meaning that different components of the application software execute on different hosts, for instance, on different computing devices, in different virtual machines, in different containers, or in different operating systems having different memory address spaces. In some embodiments, each computing device may have a single host, or a given computing device may have multiple hosts, for instance, in the case of a computing device executing multiple virtual machines, each having a virtual machine operating system and executing within an operating system of the computing device. In some cases, each host may have a different network layer host address. A "host" need not be labeled as a host in program code or data structures to constitute a host, e.g., often hosts may be labeled as "servers" or "guests."

In many cases, the application software is implemented with different application components 30 executing on the different hosts. In some cases, the different application components may communicate with one another via network messaging, for instance, via a local area network, the Internet, or a loopback network address on a given computing device. In some embodiments, the application components communicate with one another via respective application program interfaces, such as representational state transfer (REST) interfaces, for instance, in a microservices architecture. In some embodiments, each application component includes a plurality of routines, for instance, functions, methods, executables, or the like, in some cases configured to call one another. In some cases, the application components are configured to call other application components executing on other hosts, such as on other computing devices, for instance, with application program interface request including a command and parameters of the command. In some cases, some of the application components 30 may be identical to other application components on other hosts, for instance, those provided for load balancing purposes in order to concurrently service transactions. In some cases, some of the application components may be distinct from one another and serve different purposes, for instance, in different stages of a pipeline in which a transaction is processed by the distributed application. An example includes a web server that receives a request, a controller that composes a query to a database based on the request, a database that services the query and provides a query result, and a view generator that composes instructions for a web browser to render a display responsive to the request to the web server. Often, pipelines in commercial implementations are substantially more complex, for instance, including more than 10 or more than 20 stages, often with load-balancing at the various stages including more than 5 or more than 10 instances configured to service transactions at any given stage. Or some embodiments have a hub-and-spoke architecture, rather than a pipeline, or a combination thereof. In some cases, multiple software applications may be distributed across the same collection of computing devices, in some cases sharing some of the same instances of application components, and in some cases having distinct application components that are unshared.

With the complexity that can arise in distributed applications, it can be difficult to diagnose application performance issues or infrastructure issues. Accordingly, some embodiments include monitoring software. The monitoring software is of two distinct types that, while they both perform monitoring, perform functions recognized as in industry as being in distinct product categories traditionally: infrastructure monitoring, and application performance monitoring. The former can be analogized to the diagnostic software used by an automotive mechanic to monitor a car's engine, while the latter can be analogized to GPS navigation software by which a car's direction and speed is tracked. Both relate to the operation of the car, but they are distinct categories of software. A similar relationship exists for application performance monitoring and infrastructure monitoring applications.

In some embodiments, the infrastructure monitoring software may be a distributed infrastructure management application that includes the infrastructure monitor 16 and infrastructure agents 28 installed on the computing devices 20 through 24. In some embodiments, the infrastructure agent may be installed on networking equipment as well, for instance, on switches and routers. Or some embodiments are partially or entirely agentless, and metrics, events, and attributes may be gathered with the various protocols described below for this purpose.

In some embodiments, the infrastructure agent is configured to gather attributes of the computing host upon which the infrastructure agent executes, such as a host name (or other type of host identifier), a network address, a medium access control address, a domain name service, a data center identifier, a data center region, a processor model, a processor speed, amounts of processor memory of various types of cache (e.g. L1 and L2), an operating system name, an operating system version, operating system configurations, firmware names, firmware versions, driver names, driver versions, installed application names, installed application versions, amounts of memory available in random access memory, memory speed, amounts of persistent storage available, persistent storage speed, and the like. In some embodiments, the infrastructure agent is configured to gather metrics of the host upon which the infrastructure agent executes, for instance, processor utilization, memory utilization, temperature, network bandwidth, network latency, rates of packet loss on networks, and the like. In some embodiments, the infrastructure agent is configured to gather events, such as alarms, indicative of occurrences at the host upon which the infrastructure agent executes, for instance, instances of the above metrics crossing (or changing faster than) a threshold, operating system errors, crashes, reboots, corrupted memory being detected, and the like.

In some embodiments, the infrastructure agent may be configured to report such gathered information to the infrastructure monitor 16, for instance, periodically, and buffer the information between reports. In some embodiments, the infrastructure agent may be configured to receive requests for such information from the infrastructure monitor 16 and respond with responsive information, for instance, all information buffered, or information responsive to a query from the infrastructure monitor 16.

In some embodiments, the infrastructure agent 28 may include a plurality of "probes," which may be routines configured to gather information pertaining to a particular use case for the host, for example, probes configured to gather information about databases, email servers, web servers, and the like. In some embodiments, some infrastructure agents may have a plurality of probes and different infrastructure agents may have different pluralities of probes. Or in other architectures consistent with the present techniques, each "probe" may be characterized as an agent, e.g., a single host may have multiple specialized infrastructure or application performance monitoring agents.

In some use cases, system administrators do not have a way to easily take inventory of the computing devices upon which a given distributed application or plurality of distributed applications execute. Often computing devices or hosts executing thereon, are added and removed relatively frequently, often over diverse geographic areas, in some cases automatically responsive to changes in the applied load or crashes or maintenance elsewhere in the system. To ease this burden, some embodiments of the infrastructure monitor 16 are configured to automatically discover newly added hosts within a domain, for instance, new virtual machines that were added or new computing devices that were added. In some cases, the infrastructure monitor 16 may periodically, or in response to a command, scan a range of network addresses, like in a private subnet, with request sent according to various network management protocols, like Simple Network Management Protocol (SNMP), Secure Shell (SSH), Windows Management Instrumentation (WMI), or Internet Control Message Protocol (ICMP). If a computing device is not at a given address in the range, no response may be received within a threshold duration of time, and that address may be disregarded. In contrast, a new computing device or other host at a given address, upon receiving the network management protocol request may respond to the request, indicating the presence of a host. Upon detecting a new host, some embodiments of the infrastructure monitor 16 may direct the host to install an instance of the infrastructure agent and, in some cases, configure various probes thereon based upon a role indicated by the host.

In some embodiments, the infrastructure monitor 16 may receive information reported from the infrastructure agents and generate various dashboards, reports, and alarms based on this information. In some embodiments, the infrastructure monitor 16 is further configured to automatically take remedial action, for instance, provisioning additional computing devices responsive to thresholds being exceeded, like thresholds indicating CPU or memory usage greater than a threshold amount. In some embodiments, the infrastructure monitor 16 may organize the received information according to an identifier of a host upon which the infrastructure agent reporting the information is executing. Based upon discovered hosts, and in some cases information reported by those hosts, some embodiments of the infrastructure monitor 16 may construct a network-architecture topology of a physical architecture of computing devices within a domain. In some cases, this network-architecture topology may include network-architecture host identifiers for each of the hosts that were discovered or otherwise identified (for instance, manually identified and configured by a system administrator). In some cases, these host identifiers may be specified by a system administrator, or in some cases, the host itself.

In some embodiments, as discussed above, the monitoring software further includes application performance management software. For example, some embodiments may include a distributed application performance management application including the application monitor 18 and an application agent 32 (or plurality of application agents) executing on the computing devices 20 through 24. In some embodiments, the application agents may be configured to monitor performance of the application component 30. Monitoring performance may take a number of forms. Examples include measuring response times of various routines of the application component 30, for instance, durations of times elapsed between when a given routine is called and when the given routine returns a response. Other examples include gathering errors thrown by routines. In some embodiments, routines may be instrumented by adding calls to the application agent at the beginning and ends of the routines, such that the application agent receives a signal when a given routine in a given execution instance begins and ends, and the application agent may determine response times based on the signals by subtracting the time at which the begin signal was received from the time at which the end signal was received. In some embodiments, these routines may receive such signals from an operating system of a host. In some cases, the application agent and application component may be configured before both are installed on a computing device. For instance, code for the application component may be instrumented with calls to the application agent before that code is installed in a machine image or the computing device 20-24 that receives that machine image.

In some embodiments, the application agent 32 may gather attributes, metrics, and events of application components and report that gathered information to the application monitor 18, for instance, buffering the information and sending it periodically or sending the information responsive to queries. In some embodiments, the application monitor 18 may aggregate information gathered from a plurality of application agents executing on the computing devices 20 through 24 for a given distributed application and generate various dashboards, reports, and alarms. In some embodiments, the application monitor 18 may be configured to group reported metrics according to a given transaction serviced by the distributed application. For instance, a given website request and the chain of events in a pipeline by which the given website request is serviced is an example of a transaction. In many cases, the distributed application may service a relatively large number of transactions concurrently, for instance, after a relatively large number of users make requests at around the same time. Some embodiments may be configured to, for a given transaction, determine a total response time for the transaction, for instance, as perceived by a user, indicating a difference in time between when a request was received and when a response was provided for a user. Further, some embodiments may be configured to segment that response time for the transaction according to the contribution of each of the application components and routines therein. The various reports analyses, and dashboards described herein may be formed by instructing a computing device to render a graphical user interface depicting the same, for instance, by sending instructions to a web browser on a remote computing device or instructing a display of a computing device upon which the respective monitor 16 or 18 is executing. Thus, in some cases, a developer may be able to query the application monitor 18 for particularly slow transactions (or transactions for which an error occurred) and drill down into the particular application component and routine that contributed to the slow response or error.

Three user computing devices 34 are shown, but commercial implementations are expected to include substantially more, for example more than 10, more than 100, more than 100,000, or more than 1 million user computing devices, and some cases with similar numbers of concurrent sessions between the user computing devices and a distributed application constituted in part or in whole by the application components 30 described above. In some cases, the user computing devices 34 may be computing devices like those described below with reference to FIG. 4. In some embodiments, the user computing devices 34 are remote from the distributed application, for example more than a kilometer, more than 10 km, or more than 100 km away, and access the distributed application via a network 26, such as the Internet. Or in some cases, the present techniques may be applied to monolithic applications executing on a given user computing device, for example in traditional client-side executable applications like applications and a productivity suite, games, and the like.

In some embodiments, different user computing devices 34 may be concurrently accessing different services of a distributed application, for example, different webpages, different application program interface functionality, or various services in pipelines behind these entry points. In some embodiments, different ones of the user computing devices 34 may be concurrently accessing different distributed applications monitored by a software-as-a-service implementation of the monitoring application 12, infrastructure monitor 16, or application monitor 18. In some embodiments, the user computing devices 34 may be geographically distributed over a relatively large area, such as over an area greater than 100 km$^2$, like the entire United States or the world.

In some embodiments, each user computing device 34 may include an operating system in which various applications execute, including applications by which a respective user of the respective user computing device 34 interfaces with the distributed application, for example, with the client-site application providing a user interface that is formed based on commands and other data received from the server-side components of the distributed application, like in a data center. In some embodiments, each user computing device 34 includes one or more client applications 40, like a web browser or a special-purpose native application among the various types of applications described above.

In some embodiments, each of the user computing devices 34 (or a subset thereof, which is not to suggest that any other feature described herein is required in all implementations) may include a subjective-experience monitoring agent 42 executing on the user computing device 34 and implemented with program code stored in memory thereof and executed with a processor of the user computing device 34. In some embodiments, the subjective-experience monitoring agents 42 may capture data indicative of state of the client-application 40, for example, characterizing time stamped transactions in which requests were sent by the client application 40 to the application components 30, when responses were received, or transaction-traces of client-side executed routines of the client application 40.

In some embodiments, the metrics may also include those gathered by the above-described infrastructure agents except pertaining to the user computing device 34 performance. In some embodiments, the metrics may include those gathered by the above-described application agents, except pertaining to the performance of the client application 40 rather than an application component 30 executing in a data center. In some embodiments, these metrics may be gathered by a client-application state sensor 40, for example, responsive to queries to an application program interface of the operating system of the user computing device 34 for infrastructure-type metrics, or based upon instrumented code in the client application 40 reporting, for example, via a loopback address of the user computing device, when various routines of the client application 40 start and stop, or via an interface of the operating system by which resource consumption of various processes may be queried. In some embodiments, the subjective-experience monitoring agent 40 may be integrated with the client application 40, for example, executed as a background process as part of a native application or as part of client-side code executed within a web browser or browser extension.

In some embodiments, the subjective-experience monitoring agent 42 further includes a biometric interface 46 configured to obtain a data from various biometric sensors 38 positioned to capture biometric measurements of the user of the user computing device 34 while the user interfaces with the client application 40. In some embodiments, the biometric interface 46 may be configured to receive pushed events from the biometric sensors 38, for example, interrupts or other messages sent, for instance, via a networking stack of an operating system of the user computing device 34, or via a driver executing in the operating system configured to interface with various biometric sensors 38. Or in some cases, the biometric interface 46 may periodically poll the biometric sensors 38 or poll the sensors 38 in response to various events within the client application 40, for example, responsive to user engagement (like clicks, touches, speech utterances, or other UI events). For example, to conserve power and bandwidth, some embodiments may initiate such polling for some threshold duration of time after user interaction with the client application 40 is sensed, for example, for more than or less than one minute, 10 minutes, or one hour. In some cases, polling frequency may be selected based upon trade-offs between fidelity of data and consumption of battery power for the biometric sensors 38, for example, more or less often than once every 10 ms, 100 ms, one second, 10 seconds, or one minute.

In some embodiments, the biometric interface 46 may receive biometric measurements from the biometric sensors 38, in some cases in association with data that uniquely identifies the biometric sensor and indicates a type of measurement from the biometric sensor 38 and a value of a measurement of a biometric attribute. In some embodiments, values received from the biometric sensors 38 may be, for example, expressed in units that are indirectly indicative of a measurement of a biometric attribute, like a voltage, current, light intensity, or the like, that is indicative of one or more the various biometric attributes described below. Or in some cases, the measurements may be expressed in units directly descriptive of the biometric attribute, like pressure, parts-per-million, volumetric ratios, mass ratios, temperature, pulse rate, or the like. In some embodiments, the biometric sensors 38 may have been previously paired with the biometric interface 46 or otherwise registered with the biometric interface 46, and in some cases vice versa, to establish a communication channel, for example, wirelessly (e.g., via Bluetooth™, WiFi Direct™, or near-field communication NFC) or via wired connection.

Some embodiments may further include a psychometric interface 48. In some embodiments, the psychometric interface 48 may periodically, or in response to the various other types of events described above triggering biometric measurement polling or reporting, cause a user interface to be displayed overlaid on, injected within, or alongside (which is not to suggest that these categories or any other herein cannot overlap) the client application 40, with the added user interface including a user input by which the user enters their subjective assessment of their user experience, like selecting a thumbs up or thumbs down icon, a number of stars, a rating, a score from 1 to 10, turning a dial, sliding a slider, uttering a spoken characterization, gesturing with a thumbs up or down, or other form of input. In some cases, the psychometric interface may include various inputs of these kinds each corresponding to different attributes of their subjective experience, like whether they perceive their user experiences being good, responsive, confusing, enraging, and the like. Some embodiments may further include a text box user input or audio user input, by which the user may supply a prose description of what they are presently feeling in relation to the user experience with the client application 40. In some cases, the psychometric interface 48 may be presented in response to the measurements from the biometric sensors 38 triggering an alarm condition. In some cases, the gathered data from the psychometric interface 40 may be reported alongside measurements captured by the biometric interface 46 and subjected to processes like those described below with reference to the biometric data.

In some embodiments, each user computing device may be associated with a user using that computing device and one or more biometric sensors 38 configured to capture biometric measurements of biometric attributes of that respective user. For example, the two instances of user computing devices 34 include two biometric sensors 38 and three biometric sensors 38 associated with the different users. In some embodiments, a single wearable computing device may include a plurality of biosensors, like a smartwatch, a head-mounted display, or the like. Or in some cases, some or all of the biometric sensors 38 may be implemented on different computing devices, for example a separate pulse oximeter from an electroencephalograph. In some cases, some or all of the biometric sensors 38 may be integrated with the user computing device 34, for example with a camera of the user computing device 34 capturing visible or infrared biometric attributes, like facial expression or body temperature, respectively, or with a microphone capturing tone of voice or executing speech to text routines by which, for example, measures of rage or utterances like swearwords are detected.

In some embodiments, the biometric sensors 38 may include their own batter and network interfaces and communicate directly with network 26 to convey data to the monitoring application 12. Or in some cases, the biometric sensors 38 may be paired with a mobile computing device 36, like a smart phone or tablet computer that is associated with the user using a user computing device 34. In some embodiments, a native application on the mobile computing device 36 may be previously registered with a user identifier that is also supplied via the user computing device 34 to access a service of a distributed application, and some embodiments may push or pull communication with the native application on the mobile computing device 36 by accessing a user profile with a network address of the mobile computing device 36 in response to a server-side determination that the user having a corresponding user identifier has attempted to login with one of the user computing devices 34.

Or in some cases, the mobile computing device 36 may be engaged by an instance of the client application 40 executing on user computing device 34, for example, via communications on a local area network or wireless communication, like optically, audibly, with near field communication, or with Bluetooth™. In some embodiments, information about state of the client application 40 may also be captured by the mobile computing device 36, for instance, with a native application thereon executing the functionality of the subjective experience monitoring agent 42. For example, in some cases, the client application 48 may be configured to emit data indicative of his current state via ultrasonic messages, or others forms of wireless messages perceived by the mobile computing device 36. Or in some cases, client side-state may be inferred primarily or solely based on communication sent or received from server-side components of the distributed application being accessed, like a last request, a last response, or various other communications, particularly for thin client applications.

The biometric sensors 38 may sense different biometric attributes for a given user. Examples include any permutation of the following, rates of change thereof, rates of rates of change thereof: heart rate; blood pressure; cortisol level; breathing rate; electrodermal response; blood oxygen saturation; temperature; voice pitch or tone; eye gaze direction; electrical activity of a user's heart; or electrical activity of a user's brain.

The biometric sensors 38 may be any of a variety of different types of biometric sensors, including any of the following: an optical camera; an infrared camera; a depth-sensing camera; a microphone; an electroencephalograph; a pulse oximeter; an electrocardiograph; a galvanic skin response sensor; or a heart-rate sensor.

In some embodiments, different biometric measurements of different biometric attributes for a given user may be combined into a resulting biometric measurement, like a score based upon breathing rate and cortisol level. In some embodiments, combinations of biometric measurements may be selected to afford a relatively reliable indicator of various psychometric states, like rage, happiness, stress, frustration, joy, or the like. In some embodiments, such scores may be based on a weighted combination of the various input biometric measurements, and in some cases weights may be adjusted based upon data gathered by the psychometric interface, for instance, with a stochastic gradient descent adjustment of the weights configured to reduce an amount of error of psychometric predictions in a training set with paired measurement of the psychometric interface at a time that various biosensors reported data that was logged.

In some embodiments, some of the processing performed upon biometric measurements described below as implemented at user computing device 34, mobile competing device 36, or monitoring application 12 may be shifted to the biometric sensors 38 or otherwise allocated to any permutation of these computing devices. The term biometric measurement is used broadly and includes the raw signal taken from a transceiver sensing the biometric attribute, scaled and filtered versions of this signal, and binary determinations of whether the scaled and filtered version of the signal satisfies (exceeds or falls under) various thresholds. Further, the term biometric measurement includes aggregations of these types of biometric measurements, like outputs of low-pass filters calculated based on a measure of central tendency (like a mean, median, or mode, of a trailing duration of the input biometric measurement, like a trailing duration of greater than or less than one second, 10 seconds, or 10 minutes). Similarly, the term biometric measurement also includes properties of a timeseries of an input biometric measurement, like a frequency component output from a Fourier transform, a rate of change, a second order derivative, a partial derivative with respect to some other biometric measurement, a variance, a measure of central tendency, or combinations thereof (including two-way, three-way, four-way and higher order interactions).

In some embodiments, the biometric measurement is a classification of one or more input biometric measurements, for example, output by a classification tree, neural network, recurrent neural network, or the like trained to classify input biometric measurements as being indicative of various psychological states, like happy, frustrated, stressed, or the like. These and related machine learning models, in some cases, may be trained with a labeled training set gathered with both the biometric interface 46 and psychometric interface 48, for example, by iteratively adjusting model parameters to reduce an amount of distinction in the training set between a predicted classification based on the biometric measurements and a reported classification gathered via the psychometric interface 48. Similarly, for relatively high-dimensional biometric measurements, like image data and audio data, some embodiments may apply a similarly trained machine learning model to classify the input biometric measurement to output a biometric measurement. For example, some embodiments may train a deep convolution neural network to classify an image captured with a camera according to whether the image includes a face with a particular expression indicative of a psychological state.

In some embodiments, the monitoring application 12 may receive from the subjective-experience monitoring agent 42, the user's mobile computing device 36, or a biometric sensor 38 biometric measurements and, in some cases, data associated therewith indicative of client-side state of the client application 40, or in some cases client-side state may be inferred based upon messages sent or received from a server during a session. In some embodiments, client-side state may be matched to biometric measurements received by the monitoring application 12 with various techniques, for example, with a user identifier sent by the subjective-experience monitoring agent, based upon both the client application 40 and the biometric sensor or user computing device 34 or mobile computing device 36 communicating with the monitoring application 12 or the distributed application via the same public Internet protocol address, or based upon the techniques described above by which a mobile computing device 36 is paired with a client application 40 based upon a user profile.

In some embodiments, the monitoring application 12 may combine the biometric measurements with events and metrics from the infrastructure monitor 16 and application monitor 18 to improve performance of the distributed application. Improving performance may include improving subjective performance of users as reflected via the psychometric interface 48 or inferred via the biometric interface 46. Improving performance may also include improving objective performance, like latency, failure rate, bandwidth, or the like as measured by the infrastructure monitor 16 or application monitor 18. In some embodiments, improvements to objective performance may be facilitated by measurements of subjective performance, for example, a subset of the distributed application may be allocated additional resources moved away from other subsets of the distributed application in response to a measurement of sensitivity of subjective performance to objective performance of different subsets of the distributed application.

In some embodiments, the monitoring application 12 may include a subjective performance ingest module 50, an objective performance ingest module 52, a correlator module 54, a performance data repository 56, an application configuration module 60, a monitoring configuration module 58, an application configuration module 60, and a performance modulator 62. In some embodiments, these components may cooperate to execute a process described below with reference to FIG. 3 to improve performance, subjective, objective, or both, of a distributed application. In some embodiments, the monitoring application 12 may monitor subjective and objective performance of a plurality of different distributed applications, such as more than five, more than 50, or more than 500. In some embodiments, multiple tenants each having one or more of these distributed applications may access the monitoring application 12 to view reports, alarms, receive messages, and configure aspects of monitoring for distributed applications associated with the respective tenants in tenant accounts.

In some embodiments, the subjective-performance ingest module 50 may be configured to receive biometric measurements via the network 26. In some embodiments, the subjective performance ingest module 50 may perform various transformations on input biometric measurements like those described above to produce output biometric measurements. In some cases, the subjective performance ingest module 50 may periodically poll the various sources of biometric measurements described above for biometric measurement values, these values may be pushed, and in some cases, biometric measurements may be accumulated in a buffer, for example, in user computing devices 34 or mobile computing devices 36 before being conveyed to the subjective performance ingest module 50 to accumulate data during temporary periods of loss of network access. In some cases, biometric measurements may be produced by executing various transformations on received biometric measurements. In some cases, received biometric measurements may be associated with (in received communications) a distributed application, like with a distributed application identifier that distinguishes that distributed application from other distributed applications monitored by the monitoring application 12. In some embodiments, received biometric measurements may be received with an identifier of a service for which performance is described by the biometric measurement, like a service identifier that distinguishes a given service from other services of a given decentralized distributed application. In some cases, the biometric measurements may be received with a transaction identifier that distinguishes a given transaction invoking the identified service from a plurality of other transactions invoking the service, for example, a transaction in which a given user's application program interface request is serviced by calling a plurality of services in the distributed application. In some cases, the biometric measurement is received with a timestamp and a user identifier.

In some cases, baselines, thresholds for detecting anomalies, or the like are determined on user-by-user basis, based on that user's historical biometric measurements, or in some cases, such values may be determined based on a user's demographic or physical attributes, e.g., by placing users into groups on this basis, and determining baselines, thresholds for detecting anomalies, or the like for group members based on historical group biometric measurements.

In some embodiments, the objective performance ingest module 52 may receive events or metrics from the infrastructure monitor, the application monitor 18, or both. In some cases, these events or metrics may be events or metrics produced by executing various transformations on a events or metrics output by the application agents or infrastructure agents described above or output by the infrastructure monitor 16 or application monitor 18. In some cases, events or metrics may be associated with a distributed application, like with a distributed application identifier that distinguishes that distributed application from other distributed applications monitored by the monitoring application 12. In some embodiments, events or metrics may be received with an identifier of a service for which performance is described by the events or metrics, like a service identifier that distinguishes a given service from other services of a given decentralized distributed application. In some cases, the events or metrics may be received with a transaction identifier that distinguishes a given transaction invoking the identified service from a plurality of other transactions invoking the service, for example, a transaction in which a given user's application program interface request is serviced by calling a plurality of services in the distributed application. In some cases, the event or metric is received with a timestamp.

In some embodiments, the correlator 54 is configured to match events or metrics to biometric measurements, psychometric is measurements, and client-side state descriptors that correspond with one another in the sense that the events or metrics are indicative of performance of the distributed application at a time a stimulus was defined, and the psychophysical effect of that stimulus is reflected in the biometric measurements and the psychological effect is reflected in the psychometric measurements. Examples include events or metrics indicative of objective performance at a time a webpage service request was processed in a given transaction for a given service or set of services being matched to a biometric measurement and a psychometric measurement captured after the webpages rendered and displayed client-side, for instance, within a threshold duration of time, like less than one second, 10 seconds, or one minute.

Various techniques may be applied to correlate these values. In some cases, each of these values is received with the timestamp, and the values may be correlated based on timestamps, for example, with values within a threshold duration of time being paired together, values being paired with a next closest value of each type within a duration of time, or the like. In some embodiments, more descriptive information may be carried through the system to facilitate correlation. For example, in some cases, the subjective-experience monitoring agent 42 may receive a decentralized application identifier, service identifier, and transaction identifier from the client application 40, for instance, from instrumented routines therein, and the subjective-experience monitoring agent may report these identifiers in association with biometric measurements received via the biometric interface 46 within some threshold duration of time or at the time the identifiers are presented by the client application 40 to the monitor application 12. Similarly, these identifiers of client-side state may be reported via the mobile computing device 36 through wireless transmission, like ultrasonic, NFC, or optical transmission from a client application 42 the mobile computing device 36, e.g., to a camera, antenna, or microphone.

Correlation may include but does not require (which is not to suggest that any other feature is required in all implementations) determining statistical correlations between events or metrics and biometric measurements. In some cases, correlation is performed by the above-described matching operation in which reported values are correlated in time or causal relationships.

In some embodiments, the correlated values may be stored in the performance data repository 56, for example, in a plurality of performance records. In some cases, each record may include a decentralized application identifier, a service identifier, a transaction identifier, a routine identifier, a user identifier, an event or metric or plurality thereof, and a biometric measurement or plurality thereof, and a psychometric measurement or plurality thereof.

In some embodiments, the application configurator module 60 is configured to reconfigure the distributed application responsive to data stored in the performance repository 56. In some embodiments, this may include load-balancing the hosts executing the distributed application based upon performance measurements, for instance, based upon subjective performance measurements. For example, some embodiments of the application configurator module 60 may be configured to calculate respective sensitivities of psychophysical responses and psychometric responses to changes in objective performance. Some embodiments may rank the respective services (or called routines therein) according to the sensitivities and shift computing resources from services within a threshold number of positions of a bottom of the ranking to services within a threshold number of positions from a top of the ranking. In some embodiments, this may include spinning down a virtual machine or container, reimaging the virtual machine or container, spinning backup the virtual machine or container, and adding the virtual machine or container to a service discovery repository by which workload of a different service may be assigned to the virtual machine or container. Similarly, adjustments may be made to priority settings (like niceness or nice value) of processes executing various routines by which a service is implemented. In another example, application configuration may include changing a way in which data is stored, for example, increasing an amount of cache, adjusting time-to-live, provisioning computing resources with more resources, adjusting content delivery network storage, adjusting client-side caching, or the like.

In some embodiments, the monitoring configuration module 58 may adjust the parameters of the infrastructure monitor 16, the application monitor 18, or the related agents based upon the subjective performance record in the performance repository 56. For example, some embodiments may access the above-described sensitivities or records exceeding some threshold indicator of frustration or happiness to change, for example, objective performance thresholds by which various alarms are emitted or other responsive actions are taken by the infrastructure monitor 16 or application monitor 18. For example, some embodiments may determine that an additional 10 ms of latency for a given routine in a given service has zero or less than a threshold increase in an amount (e.g. frequency, count, average, or the like) of subjective performance measurements indicating frustration in the performance repository 56 and, in response, increase an objective performance threshold by 10 ms of latency in response time.

Some embodiments may deliberately perturb performance of the distributed application to probe for opportunities to reconfigure module monitoring or the application. In some embodiments, the performance modulator 62 may be configured with an inventory of services of the distributed application, and some embodiments may systematically inject latency into those services (or routines therein). For example, in some cases, the performance modulator 62 may be configured with an inventory of services and routines executed in those services in the various application components. In some embodiments, the performance modulator 62 may be called by instrumented code added to a beginning or end of each of those routines with an identifier of the respective routine, transaction, service, and distribute application. For a sampling percentage, like a randomly (e.g., pseudo-randomly) selected subset, such as less than 0.1% of transactions, the performance modulator 62 may respond to these calls with instructions to delay, for example 10 ms, or some other configurable (or systemically varied) adjustment, such as less than or more than 1 ms, 5 ms, or 100 ms. Or in some cases, these values may be stored in the various hosts and called by the respected interim instrumented code on the hosts to inject latency without introducing less controllable delays from network communications. In some embodiments, the agents on the computing devices 24 may report back to the monitoring application 12 an inventory of transaction identifiers in which latency was injected for correlation with biometric and psychometric measurements.

In some embodiments, latency may be systematically injected in every routine of every service over some duration of time for a sufficient sample size, for example, corresponding to more than 10, more than 100, or more than 1000 sessions with corresponding numbers of users, and some embodiments may measure a ratio of a change in latency to a change in an aggregate statistic of values indicative of subjective performance, like the above-describe biometric measurements or psychometric measurements. In some embodiments, the routines may be scored or ranked according to these ratios, with larger ratios, in some cases, indicating a greater sensitivity of the subjective performance to the particular routine or service. In some embodiments, the above-described load-balancing and monitoring adjustments may be applied in favor of the sensitive routines (shifting or otherwise adding resources to those process or services), and in some cases decreasing monitoring sensitivity or computing resources for the less sensitive routines.

Figure 3:
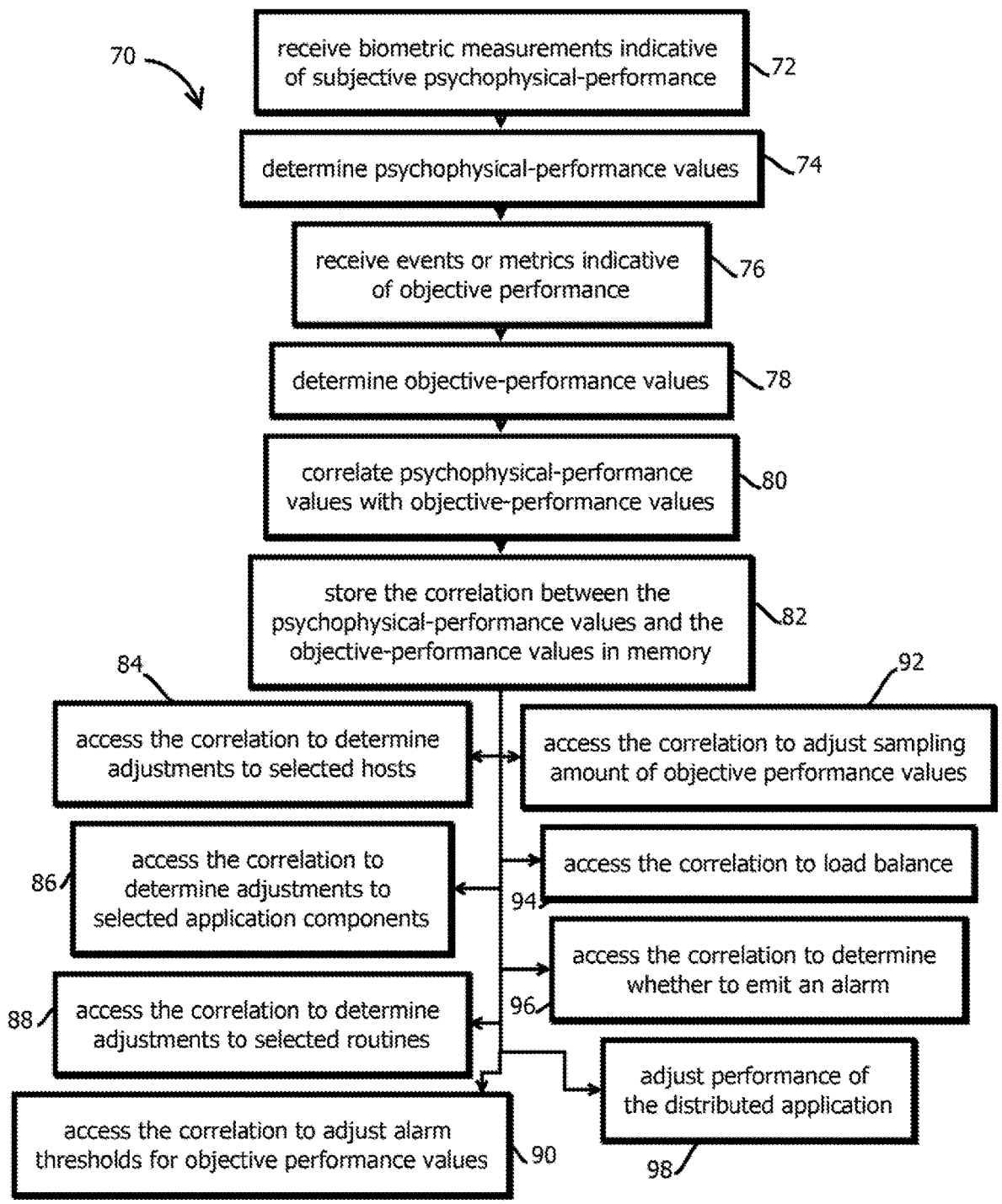
FIG. 3 is a flowchart of an example of a process to monitor psychophysical performance of distributed applications in accordance with embodiments of the present techniques.

FIG. 3 shows an example of a process 70 that may be implemented with the above-described monitoring application 12, but which is not limited to that implementation, which is not to suggest that any other feature described herein may not also be varied or omitted. In some embodiments, the functionality of the process 70 may be implemented by executing with one or more processors instructions stored on a tangible, non-transitory, machine-readable medium, which in some cases may be distributed such that different processors execute different subsets of the instructions, an implementation consistent with use of the term "medium" singular herein. In some embodiments, the illustrated instructions may be executed in a different order, may be executed concurrently or serially, and the described instructions may be replicated or omitted, which again is not to suggest that any other feature may not also be varied. In some embodiments, any subset of the illustrated operations may be performed by other participants in the computing environment 10, for example, on the user computing devices 34 or 36, the infrastructure monitor 16, the application monitor 18, or the computing devices 20 through 24.

In some embodiments, the process 70 includes receiving biometric measurements indicative of subjective psychophysical performance, as indicated by block 72. Some embodiments may then determine psychophysical performance values, as indicated by block 74. In some embodiments, this may include executing some transformation on the received values, validating the received values, filtering the received values, aggregating the received values, or passing through the received values upon determining that values that are received are indicative of psychophysical performance. Some embodiments may then receive events or metrics indicative of objective performance, as indicated by block 76. In some embodiments, the events or metrics may be those received from the infrastructure monitor 16 or the application monitor 18 described above. Some embodiments may then determine objective-performance values, as indicated by block 78. Determining objective performance values may include passing through received values upon determining that the received values pertain to objective performance, or filtering the values, normalizing the values, or otherwise transforming the values.

Some embodiments may then correlate the psychophysical-performance values with objective-performance values, as indicated by block 80. In some embodiments, this may include the operations of the above-described correlation module.

Next, some embodiments may store the correlation between the psychophysical-performance values and the objective-performance values in memory, as indicated by block 82. In some cases, this may include storing these values in the above-describe performance repository in performance records.

Some embodiments may then perform any of a variety of subsequent actions to improve performance of the distributed application. In some embodiments, this may include accessing the correlation determine adjustments to selected hosts, as indicated by block 84. In some cases, this may include changing and allocation of computing resources within a given host among various processes executing on that host, for example, changing a priority of various routines according to the above-describe sensitivities within an operating system.

Some embodiments may further access the correlation to determine adjustments to selected application components, as indicated by block 86. In some embodiments, this may include changing how data is stored to favor faster or slower data access in accordance with the techniques described above. Or in some cases, the adjustment may include adjusting where the application components run, for example, causing the application components to be spun up on other hosts with increased computing resources or decreased computing resources allocated to various services.

Some embodiments may access the correlation to determine adjustments to selected routines, as indicated by block 88. In some cases, the adjustments to selected routines may include the adjustments described above. In some cases, the adjustments may include injecting latency into the respective routine or adding or removing probes by which the routine is instrumented to increase or decrease amounts of monitoring.

In each of the above-described examples 84, 86, and 88, the operations may include selecting a host, application component, or routine. In some cases, the selection may be based upon the above-described indicators of sensitivity of subjective performance to the respective item. For example, some embodiments may rank candidates according to sensitivity and select highest or lowest candidates or those above or below some threshold ranking or those above or below a threshold sensitivity score, like above or below a threshold ratio of change in subjective performance to change in objective performance.

Some embodiments may further access the correlation to adjust alarm thresholds for objective performance values, as indicated by block 90. In some cases, this may include raising a threshold duration of time for alarm corresponding to a time for a transaction or a routine upon determining that the type of transaction or the routine does not have greater than a threshold effect on subjective performance, or vice versa. Some embodiments may similarly add or remove alarms responsive to this determination.

Some embodiments may further access the correlation to adjust sampling amounts of objective performance values, as indicated by block 92. For example, for routines, types of transactions, services, or application components that have a relatively large effect on subjective performance, some embodiments may increase a sampling percentage of objective performance measurements, or vice versa.

Some embodiments access the correlation to load balance, as indicated by block 94 and is described above.

Some embodiments may access the correlation to determine whether to emit an alarm, as indicated by block 96. For example, some embodiments may calculate a score based on both objective and subjective performance values, like a weighted sum of transaction trace latency and subjective performance values and compare that score to a threshold to determine whether to emit an alarm. Subjective performance values may be the biometric measurements or psychometric values or values based thereon indicative of subjective performance. Or some embodiments may be configured to alarm solely based on subjective indicia of performance. Emitting an alarm may include calling an API of a help-desk workload management system with a request to create a help-desk ticket for a given user exhibiting indicia of poor subjective performance. The ticket may include the above-described identifiers tying the ticket to a transaction, service, routine, distributed application, and in some cases, the user.

Some embodiments may adjust performance of the distributed application based on the correlation, as indicated by block 98. In some embodiments, this may include displaying a user interface, or sending instructions and other data by which such a user interface is remotely displayed, with the user interface presenting graphical representations of these subjective performance an objective performance of the distributed application. In some cases, the user interfaces may include dashboards, reports, and the like, by which technicians allocate resources to troubleshoot distributed applications or allocate resort computing resources to load balance or add computing resources thereto. Or in some embodiments, the adjustments may be automated, for instance with automated load balancing or elastic scaling responsive to subjective performance or values based on subjective performance exceeding are falling below some threshold.

Figure 4:
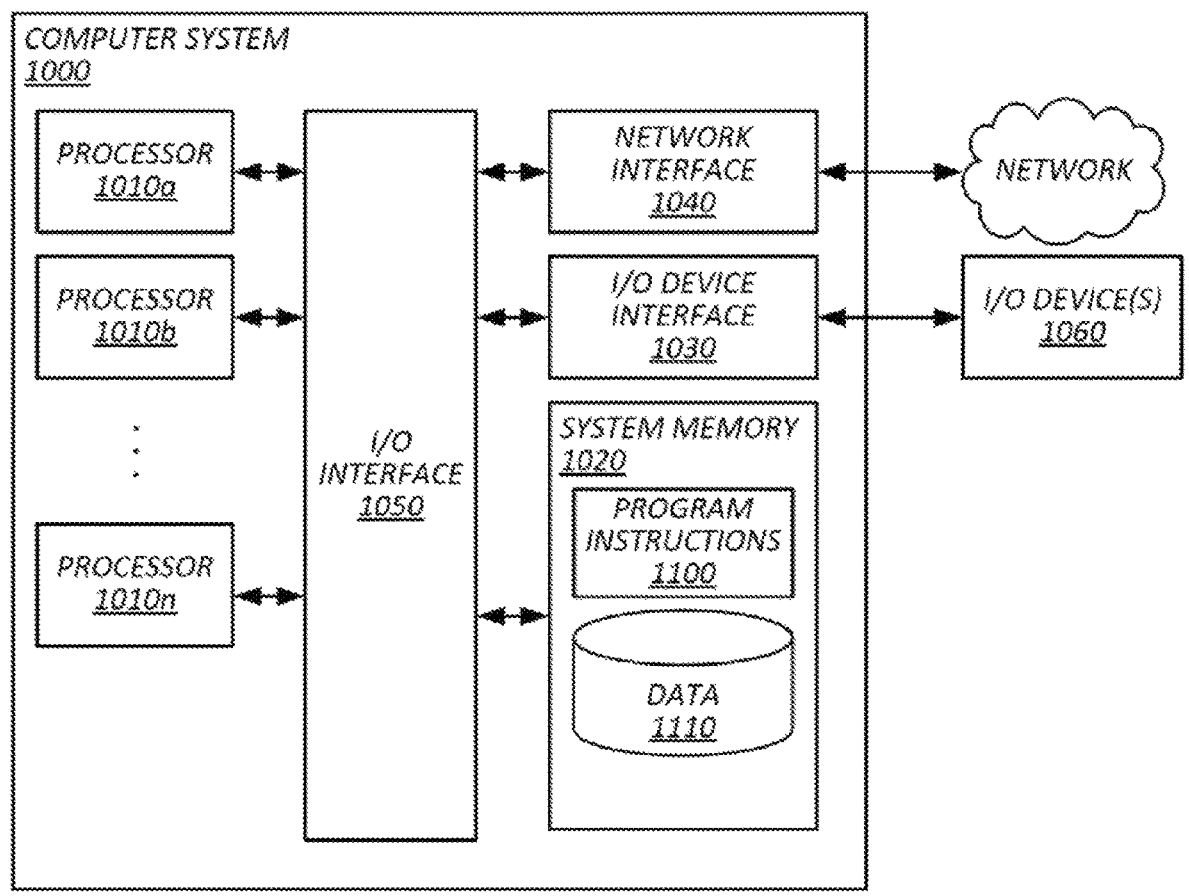
FIG. 4 is an example of a computing device by which the above techniques may be implemented.

FIG. 4 is a diagram that illustrates an exemplary computing system 1000 in accordance with embodiments of the present technique. Various portions of systems and methods described herein, may include or be executed on one or more computer systems similar to computing system 1000. Further, processes and modules described herein may be executed by one or more processing systems similar to that of computing system 1000.

Computing system 1000 may include one or more processors (e.g., processors 1010*a*-1010*n*) coupled to system memory 1020, an input/output I/O device interface 1030, and a network interface 1040 via an input/output (I/O) interface 1050. A processor may include a single processor or a plurality of processors (e.g., distributed processors). A processor may be any suitable processor capable of executing or otherwise performing instructions. A processor may include a central processing unit (CPU) that carries out program instructions to perform the arithmetical, logical, and input/output operations of computing system 1000. A processor may execute code (e.g., processor firmware, a protocol stack, a database management system, an operating system, or a combination thereof) that creates an execution environment for program instructions. A processor may include a programmable processor. A processor may include general or special purpose microprocessors. A processor may receive instructions and data from a memory (e.g., system memory 1020). Computing system 1000 may be a uni-processor system including one processor (e.g., processor 1010*a*), or a multi-processor system including any number of suitable processors (e.g., 1010*a*-1010*n*). Multiple processors may be employed to provide for parallel or sequential execution of one or more portions of the techniques described herein. Processes, such as logic flows, described herein may be performed by one or more programmable processors executing one or more computer programs to perform functions by operating on input data and generating corresponding output. Processes described herein may be performed by, and apparatus can also be implemented as, special purpose logic circuitry, e.g., an FPGA (field programmable gate array) or an ASIC (application specific integrated circuit). Computing system 1000 may include a plurality of computing devices (e.g., distributed computer systems) to implement various processing functions.

I/O device interface 1030 may provide an interface for connection of one or more I/O devices 1060 to computer system 1000. I/O devices may include devices that receive input (e.g., from a user) or output information (e.g., to a user). I/O devices 1060 may include, for example, graphical user interface presented on displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, or the like. I/O devices 1060 may be connected to computer system 1000 through a wired or wireless connection. I/O devices 1060 may be connected to computer system 1000 from a remote location. I/O devices 1060 located on remote computer system, for example, may be connected to computer system 1000 via a network and network interface 1040.

Network interface 1040 may include a network adapter that provides for connection of computer system 1000 to a network. Network interface may 1040 may facilitate data exchange between computer system 1000 and other devices connected to the network. Network interface 1040 may support wired or wireless communication. The network may include an electronic communication network, such as the Internet, a local area network (LAN), a wide area network (WAN), a cellular communications network, or the like.

System memory 1020 may be configured to store program instructions 1100 or data 1110. Program instructions 1100 may be executable by a processor (e.g., one or more of processors 1010a-1010n) to implement one or more embodiments of the present techniques. Instructions 1100 may include modules of computer program instructions for implementing one or more techniques described herein with regard to various processing modules. Program instructions may include a computer program (which in certain forms is known as a program, software, software application, script, or code). A computer program may be written in a programming language, including compiled or interpreted languages, or declarative or procedural languages. A computer program may include a unit suitable for use in a computing environment, including as a stand-alone program, a module, a component, or a subroutine. A computer program may or may not correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one or more computer processors located locally at one site or distributed across multiple remote sites and interconnected by a communication network.

System memory 1020 may include a tangible program carrier having program instructions stored thereon. A tangible program carrier may include a non-transitory computer readable storage medium. A non-transitory computer readable storage medium may include a machine readable storage device, a machine readable storage substrate, a memory device, or any combination thereof. Non-transitory computer readable storage medium may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. System memory 1020 may include a non-transitory computer readable storage medium that may have program instructions stored thereon that are executable by a computer processor (e.g., one or more of processors 1010a-1010n) to cause the subject matter and the functional operations described herein. A memory (e.g., system memory 1020) may include a single memory device and/or a plurality of memory devices (e.g., distributed memory devices). Instructions or other program code to provide the functionality described herein may be stored on a tangible, non-transitory computer readable media. In some cases, the entire set of instructions may be stored concurrently on the media, or in some cases, different parts of the instructions may be stored on the same media at different times, e.g., a copy may be created by writing program code to a first-in-first-out buffer in a network interface, where some of the instructions are pushed out of the buffer before other portions of the instructions are written to the buffer, with all of the instructions residing in memory on the buffer, just not all at the same time.

I/O interface 1050 may be configured to coordinate I/O traffic between processors 1010a-1010n, system memory 1020, network interface 1040, I/O devices 1060, and/or other peripheral devices. I/O interface 1050 may perform protocol, timing, or other data transformations to convert data signals from one component (e.g., system memory 1020) into a format suitable for use by another component (e.g., processors 1010a-1010n). I/O interface 1050 may include support for devices attached through various types of peripheral buses, such as a variant of the Peripheral Component Interconnect (PCI) bus standard or the Universal Serial Bus (USB) standard.

Embodiments of the techniques described herein may be implemented using a single instance of computer system 1000 or multiple computer systems 1000 configured to host different portions or instances of embodiments. Multiple computer systems 1000 may provide for parallel or sequential processing/execution of one or more portions of the techniques described herein.

Those skilled in the art will appreciate that computer system 1000 is merely illustrative and is not intended to limit the scope of the techniques described herein. Computer system 1000 may include any combination of devices or software that may perform or otherwise provide for the performance of the techniques described herein. For example, computer system 1000 may include or be a combination of a cloud-computing system, a data center, a server rack, a server, a virtual server, a desktop computer, a laptop computer, a tablet computer, a server device, a client device, a mobile telephone, a personal digital assistant (PDA), a mobile audio or video player, a game console, a vehicle-mounted computer, or a Global Positioning System (GPS), or the like. Computer system 1000 may also be connected to other devices that are not illustrated, or may operate as a stand-alone system. In addition, the functionality provided by the illustrated components may in some embodiments be combined in fewer components or distributed in additional components. Similarly, in some embodiments, the functionality of some of the illustrated components may not be provided or other additional functionality may be available.

Those skilled in the art will also appreciate that while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 1000 may be transmitted to computer system 1000 via transmission media or signals such as electrical, electromagnetic, or digital signals, conveyed via a communication medium such as a network or a wireless link. Various embodiments may further include receiving, sending, or storing instructions or data implemented in accordance with the foregoing description upon a computer-accessible medium. Accordingly, the present techniques may be practiced with other computer system configurations.

In block diagrams, illustrated components are depicted as discrete functional blocks, but embodiments are not limited to systems in which the functionality described herein is organized as illustrated. The functionality provided by each of the components may be provided by software or hardware modules that are differently organized than is presently depicted, for example such software or hardware may be intermingled, conjoined, replicated, broken up, distributed (e.g. within a data center or geographically), or otherwise differently organized. The functionality described herein may be provided by one or more processors of one or more computers executing code stored on a tangible, non-transitory, machine readable medium. In some cases, notwithstanding use of the singular term "medium," the instructions may be distributed on different storage devices associated with different computing devices, for instance, with each computing device having a different subset of the instructions, an implementation consistent with usage of the singular term "medium" herein. In some cases, third party content delivery networks may host some or all of the information conveyed over networks, in which case, to the extent information (e.g., content) is said to be supplied or otherwise provided, the information may be provided by sending instructions to retrieve that information from a content delivery network.

The reader should appreciate that the present application describes several techniques. Rather than separating those techniques into multiple isolated patent applications, applicants have grouped these techniques into a single document because their related subject matter lends itself to economies in the application process. But the distinct advantages and aspects of such techniques should not be conflated. In some cases, embodiments address all of the deficiencies noted herein, but it should be understood that the techniques are independently useful, and some embodiments address only a subset of such problems or offer other, unmentioned benefits that will be apparent to those of skill in the art reviewing the present disclosure. Due to costs constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative only and are for the purpose of teaching those skilled in the art the general manner of carrying out the techniques. It is to be understood that the forms of the techniques shown and described herein are to be taken as examples of embodiments. Elements and materials may be substituted for those illustrated and described herein, parts and processes may be reversed or omitted, and certain features of the techniques may be utilized independently, all as would be apparent to one skilled in the art after having the benefit of this description of the techniques. Changes may be made in the elements described herein without departing from the spirit and scope of the techniques as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Further, unless otherwise indicated, statements that one value or action is "based on" another condition or value encompass both instances in which the condition or value is the sole factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device.

In this patent, certain U.S. patents, U.S. patent applications, or other materials (e.g., articles) have been incorporated by reference. The text of such U.S. patents, U.S. patent applications, and other materials is, however, only incorporated by reference to the extent that no conflict exists between such material and the statements and drawings set forth herein. In the event of such conflict, the text of the present document governs.

The present techniques will be better understood with reference to the following enumerated embodiments:

1. A method, comprising: receiving, with one or more processors executing at least part of a monitoring application, via a network, biometric measurements, wherein: the monitoring application is configured to monitor performance of a distributed application or performance of one or more network hosts upon which at least part of the distributed application executes, the distributed application is configured to provide services to user computing devices via the network, the distributed application comprises a plurality of application components executing on a plurality of different network hosts, the application components comprise a plurality of routines defined by program code of the distributed application, the biometric measurements are respective measurements of a biometric attribute of a plurality of respective users operating a plurality of respective user computing devices accessing at least some of the services provided by the distributed application, different respective users have different respective biometric measurements among the received biometric measurements, and the biometric measurements are indicative of psychophysical performance of the distributed application as exhibited by the plurality of users; receiving, with one or more processors executing at least part of the monitoring application, from application components or network hosts, events or metrics indicative of objective performance of the network hosts or the routines, wherein the events or metrics are indicative of objective performance during a duration of time when stimuli to which the biometric measurements are responsive are at least partially defined by the distributed application; correlating psychophysical-performance values based on the biometric measurements indicative of psychophysical performance with objective-performance values based on the events or metrics indicative of objective performance; storing the correlation between the psychophysical-performance values and the objective-performance values in memory; and accessing the correlation to select hosts, application components, or routines to be adjusted to improve objective performance of the distributed application or psychophysical performance of the distributed application.

2. The method of embodiment 1, wherein accessing the correlation to select hosts, application components, or routines to be adjusted to improve objective performance of the distributed application or psychophysical performance of the distributed application comprises: determining that psychophysical performance of the distributed application is impaired based on both the biometric measurements and the events or metrics indicative of performance of the network hosts or the routines; and selecting a subset of the distributed application contributing to the impaired performance to indicate whether to adjust network hosts, application components, or routines of the distributed application to improve psychophysical performance of the distributed application.

3. The method of any one of embodiments 1-2, wherein the biometric measurements include measurement of at least one of the following types of biometric attributes: heart rate; blood pressure; cortisol level; breathing rate; electrodermal response; blood oxygen saturation; temperature; voice pitch or tone; eye gaze direction; electrical activity of a user's heart; or electrical activity of a user's brain.

4. The method of any one of embodiments 1-3, wherein the biometric measurements are obtained from at least three of the following types of biometric sensors, with different users being measured by at least some sensors that are of a different type from sensors used to measure other users: an optical camera; an infrared camera; a depth-sensing camera; a microphone; an electroencephalograph; a pulse oximeter; an electrocardiograph; a galvanic skin response sensor; or a heart-rate sensor.

5. The method of any one of embodiments 1-4, wherein: the biometric measurements include a first biometric measurement of a first user among the plurality of users; the first biometric measurement is from a wearable computing device worn by the first user sensing the biometric attribute of the first user concurrent with the first user accessing a first service among the services with a first computing device; the first biometric measurement is received with data by which the first biometric measurement is associated with an identifier of the distributed application and a subset of the services provided by the distributed application; and the identifier of the distributed application distinguishes the distributed application from a plurality of other distributed applications monitored by the monitoring application.

6. The method of embodiment 5, wherein the data by which the first biometric measurement is associated with an identifier of the distributed application comprises: a network address through which both at least some of the services are provided to the first computing device of the first user by the distributed application and a network address through which the first biometric measurement is conveyed to the monitoring application.

7. The method of any one of embodiments 5-6, wherein: the data by which the first biometric measurement is associated with an identifier of the distributed application comprises a message from an agent executing on the first computing device of the user; the first biometric measurement is received from the wearable computing device by the agent; the first biometric measurement is caused to be sent to the monitoring application by the agent; the agent is configured to determine, based on a state of a client-side application of the first computing device, a first service identifier that distinguishes the first service from other services of the distributed application; the agent is configured to cause the first service identifier to be sent to the monitoring application; the first biometric measurement is received by the monitoring application with data that associates the first biometric measurement with the first service identifier; and accessing the correlation to select hosts, application components, or routines to be adjusted to improve objective performance of the distributed application or psychophysical performance of the distributed application comprises determining that the first service has exhibited impaired performance based on the correlation and the first service identifier.

8. The method of any one of embodiments 5-7, wherein: the data by which the first biometric measurement is associated with an identifier of the distributed application comprises a first service identifier wirelessly received by the wearable computing device or a mobile computing device of the first user from the first computing device and caused to be sent by the wearable computing device or the mobile computing device of the first user to the monitoring application; and accessing the correlation to select hosts, application components, or routines to be adjusted to improve objective performance of the distributed application or psychophysical performance of the distributed application comprises determining that the first service has not exhibited impaired performance and determining that a second service among the services has exhibited impaired performance.

9. The method of any one of embodiments 5-8, wherein: the biometric measurements include a second biometric measurement of a second user among the plurality of users; the second biometric measurement is from a second wearable computing device worn by the second user sensing the biometric attribute of the second user concurrent with the second user accessing the first service among the services with a second computing device; the second biometric measurement is received with data by which the second biometric measurement is associated with an identifier of the distributed application and an identifier of the first service; and the identifier of the distributed application distinguishes the distributed application from a plurality of other distributed applications monitored by the monitoring application; the identifier of the first service distinguishes the first services from other services among the services provided by the distributed application; and correlating psychophysical-performance values with objective-performance values comprises determining a psychophysical-performance value based on an aggregate statistic of psychophysical-performance of the first service based on both the first biometric measurement and the second biometric measurement.

10. The method of any one of embodiments 1-9, wherein: accessing the correlation to select hosts, application components, or routines to be adjusted to improve objective performance of the distributed application or psychophysical performance of the distributed application comprises: determining, for each of the routines, a respective measure of sensitivity of change in of psychophysical-performance to change in objective-performance of the respective routine by modulating objective-performance of the respective routine.

11. The method of embodiment 10, wherein determining, for each of the plurality of the routines, the respective measure of sensitivity of change in of psychophysical-performance to change in objective-performance of the respective routine comprises determining, for a given routine, for each of a plurality of services among the services provided by the distributed application, a respective service-specific measure of sensitivity of change in of psychophysical-performance to change in objective-performance of the given routine.

12. The method of any one of embodiments 1-11, comprising: accessing, for a given user among the plurality of users, a time-series of biometric measurements; determining, based on the time-series, a measure of variation of the biometric attribute for the given user; and determining that a new biometric measurement is anomalous by comparing the new measurement to a threshold determined based on the measure of variation.

13. The method of any one of embodiments 1-12, comprising: adjusting an objective-performance alarm threshold based on the psychophysical-performance values.

14. The method of any one of embodiments 1-13, comprising: load balancing based on the psychophysical-performance values.

15. The method of any one of embodiments 1-14, comprising: providing the services with the distributed application.

16. A tangible, non-transitory, machine-readable medium storing instructions that when executed by a data processing apparatus cause the data processing apparatus to perform operations comprising: the operations of any of embodiments 1-15.

17. A system, comprising: one or more processors; and memory storing instructions that when executed by the processors cause the processors to effectuate operations comprising: the operations of any of embodiments 1-15.

What is claimed is:

1. A method, comprising:
receiving, with one or more processors executing at least part of a monitoring application, via a network, biometric measurements, wherein:
the monitoring application is configured to monitor performance of a distributed application or performance of one or more network hosts upon which at least part of the distributed application executes,
the distributed application is configured to provide services to user computing devices via the network,
the distributed application comprises a plurality of application components executing on a plurality of different network hosts,
the application components comprise a plurality of routines defined by program code of the distributed application,
the biometric measurements are respective measurements of a biometric attribute of a plurality of respective users operating a plurality of respective user computing devices accessing at least some of the services provided by the distributed application,
different respective users have different respective biometric measurements among the received biometric measurements, and
the biometric measurements are indicative of psychophysical performance of the distributed application as exhibited by the plurality of users;
receiving, with one or more processors executing at least part of the monitoring application, from application components or network hosts, events or metrics indicative of objective performance of the network hosts or the routines, wherein the events or metrics are indicative of objective performance during a duration of time when stimuli to which the biometric measurements are responsive are at least partially defined by the distributed application;
correlating psychophysical-performance values based on the biometric measurements indicative of psychophysical performance with objective-performance values based on the events or metrics indicative of objective performance;
storing the correlation between the psychophysical-performance values and the objective-performance values in memory; and
accessing the correlation to select hosts, application components, or routines to be adjusted to improve objective performance of the distributed application or psychophysical performance of the distributed application.

2. The method of claim 1, wherein accessing the correlation to select hosts, application components, or routines to be adjusted to improve objective performance of the distributed application or psychophysical performance of the distributed application comprises:
determining that psychophysical performance of the distributed application is impaired based on both the biometric measurements and the events or metrics indicative of performance of the network hosts or the routines; and
selecting a subset of the distributed application contributing to the impaired performance to indicate whether to adjust network hosts, application components, or routines of the distributed application to improve psychophysical performance of the distributed application.

3. The method of claim 1, wherein the biometric measurements include measurement of at least one of the following types of biometric attributes:
   heart rate;
   blood pressure;
   cortisol level;
   breathing rate;
   electrodermal response;
   blood oxygen saturation;
   temperature;
   voice pitch or tone;
   eye gaze direction;
   electrical activity of a user's heart; or
   electrical activity of a user's brain.

4. The method of claim 1, wherein the biometric measurements are obtained from at least three of the following types of biometric sensors, with different users being measured by at least some sensors that are of a different type from sensors used to measure other users:
   an optical camera;
   an infrared camera;
   a depth-sensing camera;
   a microphone;
   an electroencephalograph;
   a pulse oximeter;
   an electrocardiograph;
   a galvanic skin response sensor; or
   a heart-rate sensor.

5. The method of claim 1, wherein:
   the biometric measurements include a first biometric measurement of a first user among the plurality of users;
   the first biometric measurement is from a wearable computing device worn by the first user sensing the biometric attribute of the first user concurrent with the first user accessing a first service among the services with a first computing device;
   the first biometric measurement is received with data by which the first biometric measurement is associated with an identifier of the distributed application and a subset of the services provided by the distributed application; and
   the identifier of the distributed application distinguishes the distributed application from a plurality of other distributed applications monitored by the monitoring application.

6. The method of claim 5, wherein the data by which the first biometric measurement is associated with an identifier of the distributed application comprises:
   a network address through which both at least some of the services are provided to the first computing device of the first user by the distributed application and a network address through which the first biometric measurement is conveyed to the monitoring application.

7. The method of claim 5, wherein:
   the data by which the first biometric measurement is associated with an identifier of the distributed application comprises a message from an agent executing on the first computing device of the user;
   the first biometric measurement is received from the wearable computing device by the agent;
   the first biometric measurement is caused to be sent to the monitoring application by the agent;
   the agent is configured to determine, based on a state of a client-side application of the first computing device, a first service identifier that distinguishes the first service from other services of the distributed application;
   the agent is configured to cause the first service identifier to be sent to the monitoring application;
   the first biometric measurement is received by the monitoring application with data that associates the first biometric measurement with the first service identifier; and
   accessing the correlation to select hosts, application components, or routines to be adjusted to improve objective performance of the distributed application or psychophysical performance of the distributed application comprises determining that the first service has exhibited impaired performance based on the correlation and the first service identifier.

8. The method of claim 5, wherein:
   the data by which the first biometric measurement is associated with an identifier of the distributed application comprises a first service identifier wirelessly received by the wearable computing device or a mobile computing device of the first user from the first computing device and caused to be sent by the wearable computing device or the mobile computing device of the first user to the monitoring application; and
   accessing the correlation to select hosts, application components, or routines to be adjusted to improve objective performance of the distributed application or psychophysical performance of the distributed application comprises determining that the first service has not exhibited impaired performance and determining that a second service among the services has exhibited impaired performance.

9. The method of claim 5, wherein:
   the biometric measurements include a second biometric measurement of a second user among the plurality of users;
   the second biometric measurement is from a second wearable computing device worn by the second user sensing the biometric attribute of the second user concurrent with the second user accessing the first service among the services with a second computing device;
   the second biometric measurement is received with data by which the second biometric measurement is associated with an identifier of the distributed application and an identifier of the first service; and
   the identifier of the distributed application distinguishes the distributed application from a plurality of other distributed applications monitored by the monitoring application;
   the identifier of the first service distinguishes the first services from other services among the services provided by the distributed application; and
   correlating psychophysical-performance values with objective-performance values comprises determining a psychophysical-performance value based on an aggregate statistic of psychophysical-performance of the first service based on both the first biometric measurement and the second biometric measurement.

10. The method of claim 1, wherein:
    accessing the correlation to select hosts, application components, or routines to be adjusted to improve objective performance of the distributed application or psychophysical performance of the distributed application comprises:

determining, for each of the routines, a respective measure of sensitivity of change in of psychophysical-performance to change in objective-performance of the respective routine by modulating objective-performance of the respective routine.

11. The method of claim 10, wherein determining, for each of the plurality of routines, the respective measure of sensitivity of change in of psychophysical-performance to change in objective-performance of the respective routine comprises
determining, for a given routine, for each of a plurality of services among the services provided by the distributed application, a respective service-specific measure of sensitivity of change in of psychophysical-performance to change in objective-performance of the given routine.

12. The method of claim 1, comprising:
accessing, for a given user among the plurality of users, a time-series of biometric measurements;
determining, based on the time-series, a measure of variation of the biometric attribute for the given user; and
determining that a new biometric measurement is anomalous by comparing the new measurement to a threshold determined based on the measure of variation.

13. The method of claim 1, comprising:
adjusting an objective-performance alarm threshold based on the psychophysical-performance values.

14. The method of claim 1, comprising:
load balancing based on the psychophysical-performance values.

15. The method of claim 1, comprising:
steps for monitoring infrastructure; and
steps for monitoring application performance,
wherein correlating psychophysical-performance values with objective-performance values comprises steps for correlating psychophysical-performance values with objective-performance values.

16. The method of claim 1, comprising:
providing the services with the distributed application.

17. A tangible, non-transitory, machine-readable medium storing instructions that when executed by one or more processors effectuate operations comprising:
receiving, with one or more processors executing at least part of a monitoring application, via a network, biometric measurements, wherein:
the monitoring application is configured to monitor performance of a distributed application or performance of one or more network hosts upon which at least part of the distributed application executes,
the distributed application is configured to provide services to user computing devices via the network,
the distributed application comprises a plurality of application components executing on a plurality of different network hosts,
the application components comprise a plurality of routines defined by program code of the distributed application,
the biometric measurements are respective measurements of a biometric attribute of a plurality of respective users operating a plurality of respective user computing devices accessing at least some of the services provided by the distributed application,
different respective users have different respective biometric measurements among the received biometric measurements, and
the biometric measurements are indicative of psychophysical performance of the distributed application as exhibited by the plurality of users;
receiving, with one or more processors executing at least part of the monitoring application, from application components or network hosts, events or metrics indicative of objective performance of the network hosts or the routines, wherein the events or metrics are indicative of objective performance during a duration of time when stimuli to which the biometric measurements are responsive are at least partially defined by the distributed application;
correlating psychophysical-performance values based on the biometric measurements indicative of psychophysical performance with objective-performance values based on the events or metrics indicative of objective performance;
storing the correlation between the psychophysical-performance values and the objective-performance values in memory; and
accessing the correlation to select hosts, application components, or routines to be adjusted to improve objective performance of the distributed application or psychophysical performance of the distributed application.

18. The medium of claim 17, wherein accessing the correlation to select hosts, application components, or routines to be adjusted to improve objective performance of the distributed application or psychophysical performance of the distributed application comprises:
determining that psychophysical performance of the distributed application is impaired based on both the biometric measurements and the events or metrics indicative of performance of the network hosts or the routines; and
selecting a subset of the distributed application contributing to the impaired performance to indicate whether to adjust network hosts, application components, or routines of the distributed application to improve psychophysical performance of the distributed application.

19. The medium of claim 17, wherein:
the biometric measurements include measurement of at least two of the following types of biometric attributes:
heart rate;
blood pressure;
cortisol level;
breathing rate;
electrodermal response;
blood oxygen saturation;
temperature;
voice pitch or tone;
eye gaze direction;
electrical activity of a user's heart; or
electrical activity of a user's brain; and
the biometric measurements are obtained from at least two of the following types of biometric sensors, with different users being measured by at least some sensors that are of a different type from sensors used to measure other users:
an optical camera;
an infrared camera;
a depth-sensing camera;
a microphone;
an electroencephalograph;
a pulse oximeter;
an electrocardiograph;
a galvanic skin response sensor; or
a heart-rate sensor.

20. The medium of claim 17, the operations comprising:
adjusting an objective-performance alarm threshold based on the psychophysical-performance values; and
load balancing based on the psychophysical-performance values.

* * * * *